US009442051B2

(12) United States Patent
Wang

(10) Patent No.: US 9,442,051 B2
(45) Date of Patent: Sep. 13, 2016

(54) METHODS TO ACCELERATE THE BINDING OF BIOLOGICAL MOLECULES

(71) Applicant: Yingjian Wang, Holden, MA (US)

(72) Inventor: Yingjian Wang, Holden, MA (US)

(*) Notice: Subject to any disclaimer, the term of this patent is extended or adjusted under 35 U.S.C. 154(b) by 566 days.

(21) Appl. No.: 13/913,581

(22) Filed: Jun. 10, 2013

(65) Prior Publication Data
US 2014/0363897 A1    Dec. 11, 2014

(51) Int. Cl.
*G01N 33/566*  (2006.01)
*G01N 1/34*  (2006.01)
*G01N 1/40*  (2006.01)
*G01N 33/543*  (2006.01)

(52) U.S. Cl.
CPC ............. *G01N 1/34* (2013.01); *G01N 1/405* (2013.01); *G01N 33/54393* (2013.01); *Y10T 436/255* (2015.01)

(58) Field of Classification Search
CPC .. G01N 35/10; G01N 33/50; G01N 35/1002; G01N 33/5306; G01N 38/00; G01N 33/582; G01N 33/558; C12Q 1/6837; B01J 3/50255
USPC .......................................... 422/509; 436/501
See application file for complete search history.

(56) References Cited

U.S. PATENT DOCUMENTS

| | | | | |
|---|---|---|---|---|
| 4,366,241 A | * | 12/1982 | Tom ..................... | G01N 33/558 422/412 |
| 4,632,241 A | * | 12/1986 | Brough .................. | A47F 7/163 190/1 |
| 5,155,049 A | * | 10/1992 | Kauvar ................. | B01D 57/02 204/464 |
| 7,838,222 B2 | * | 11/2010 | Knezevic ............. | B01J 19/0046 435/6.19 |
| 8,557,600 B2 | * | 10/2013 | Mabuchi ............. | B01L 3/50255 422/536 |
| 9,023,766 B2 | * | 5/2015 | Wang .................. | C12Q 1/6837 435/7.1 |
| 2002/0197631 A1 | * | 12/2002 | Lawrence ............... | B01L 3/502 435/270 |
| 2003/0099927 A1 | * | 5/2003 | Wang ................... | C12Q 1/6837 506/9 |
| 2008/0118983 A1 | * | 5/2008 | Wang ............... | G01N 27/44739 436/63 |
| 2012/0202709 A1 | * | 8/2012 | Bergo ..................... | C40B 30/10 506/12 |
| 2012/0252000 A1 | * | 10/2012 | Cohen ................. | G01N 33/689 435/2 |

* cited by examiner

Primary Examiner — Nina Bhat
(74) Attorney, Agent, or Firm — Mirick O'Connell, LLP

(57) ABSTRACT

A method is provided for enhancing the binding of reagents to ligands. In the method a ligand is immobilized on a porous support and incubated with a reagent solution. The binding of the reagent to the ligand is increased by a cycling process of passing the reagent solution through the support multiple times. A device that facilitates the cycling process is disclosed. Provided is a method to detect multiple ligands using the cycling process.

20 Claims, 4 Drawing Sheets

METHODS TO ACCELERATE THE BINDING OF BIOLOGICAL MOLECULES

BACKGROUND

Proteins are important components of cells and their activities determine various cellular functions. All diseases associate with some changes in protein expressions; therefore, comparison of the protein expressions between normal and abnormal biological samples are useful for understanding disease mechanisms and clinical diagnostics.

Proteins can be detected by immunological methods, such as Western blotting and Enzyme-Linked Immunosorbent Assay (ELISA). Western blotting (Immunoblotting) is a widely used technique in protein research. It combines the resolution of gel electrophoresis with the specificity of immunochemical detection and is powerful in determining a number of important characteristics of protein antigens, e.g., the relative molecular weight and the quantity of an antigen in a protein sample. When combined with immunoprecipitation, Western blotting allows the detection of specific interactions between proteins. It is also useful in detecting protein posttranslational modifications, e.g., protein tyrosine phosphorylation (Kamps, 1991. *Methods Enzymol* 201:101-10). Protein arrays have been used for examining protein expression, protein phosphorylation, protein-protein interaction, protein-DNA interaction, and protein-analyte interaction (Lueking et al. 1999 Anal. Biochem. 270, 103-111. Wang et al. 2000 Mol. Cell Biol. 20, 4505). Immunochemical staining is another versatile technique in determining both the presence and localization of proteins (Harlow and Lane, Antibodies, a laboratory manual, Cold Spring Harbor Press, 1988). An antibody array-based staining method was also developed for examining protein expression, protein cellular and subcellular localization, and other properties (Wang, 2004. Proteomics 4, 20-26).

Many protein immunodetection methods involve the interaction of a reagent (e.g. antibody) and a ligand (e.g. a protein) immobilized on a solid support, such as a membrane or a multi-well plate. In most cases, the binding occurs during the incubation of the ligand-bound support in the reagent solution. For example, a standard procedure for Western blotting includes the steps of separating proteins by gel electrophoresis, transferring proteins from a gel to a membrane support, and sequential incubation of the blot membrane in blocking, washing, and antibody solutions.

In general, the immunodetection is a process involving multiple changes of solutions, and is usually extended over several hours. A key but time-consuming step is the binding of an antibody to its antigen. Several factors influence the time taken to reach binding equilibrium, including the rate of diffusion and the affinity of the antibody for the antigen. It is desirable to accelerate the process to save time.

After their formation, the antibody-antigen complexes should be maintained till the end of the assay. However, because antibody-antigen interactions are reversible, the subsequent washing and incubation could lead to significant dissociation of the antibody-antigen complexes. Therefore, it is also critical to shorten the assay process in order to maximize the antibody-antigen binding.

Accelerated assay procedure is desirable in many applications. For example, a fast assay format makes it possible to use the assay in applications requiring results in rush. Several strategies have been used to facilitate antibody-antigen binding and shorten immuno-detection process. For example, agitation, usually by shaking, is routinely used to accelerate antibody diffusion, thereby its binding to antigen.

A vacuum-assisted filtration-like process was used in The SNAP i.d.™ system from Millipore, which claims that it can shorten the Western blotting procedure from several hours to less than 45 minutes. Filtration is a commonly used method for the separation of solids from fluids by passing the fluids through filter(s), such as a porous membrane. Oversize solids in the fluid are retained. Filtration devices comprising various components are well known. Many device designs have been made for filtration process; widely used to clarify and sterilize biological solutions, such as fetal calf serum, tissue culture media and the like. Vacuum-assisted filtration-like process has been used in immobilizing proteins and nucleic acids on a membrane support; and in purifying DNA. For examples, the 96-well Bio-Dot® and 48-well Bio-Dot SF microfiltration units from Bio-Rad are used for binding proteins or nucleic acids in solution onto membranes.

Besides SNAP i.d, several other prior arts also described methods of passing fluid through a membrane in immunoassays. For example, U.S. Pat. Nos. 4,366,241 and 4,632,901 describes using the capillary action of an absorbent material to draw fluids through a reaction-supporting membrane. U.S. Pat. No. 5,155,049 described another technique for passing liquid through a membrane.

There are limitations when a filtration-like process is used in reagent-ligand binding. Particularly, because one passage is usually insufficient for maximum binding, the existing methods do not provide optimal conditions for maximum binding. Therefore, there is a need for improved methods to increase binding.

In many applications it is usually necessary to probe multiple sample membranes. For example, it is often necessary to probe multiple western blot membranes when a large number of protein samples are studied. In clinic applications, it is often needed to screen many patient samples for the same biomarker. Therefore, there is a need for fast, easy simultaneous detection of ligands on multiple porous membranes.

PURPOSE OF THE INVENTION

It is an object of the present invention to describe a method to facilitate the binding of a reagent to a ligand immobilized on a porous support. In particular the invention teaches the use of multiple cycles of passing reagent solutions through the ligand-immobilized porous support.

It is also an object of the invention to provide a device having means to produce multiple cycles of reagent solution through ligand-immobilized porous support.

It is further an object of the invention to teach a method to allow the binding of a reagent solution to a ligand that are immobilized on multiple porous supports that are stacked.

Further objects and features of the invention will become apparent from a consideration of the ensuring description.

SUMMARY

The invention provides a method for facilitating the binding of reagents to ligands immobilized on a porous support. In the method, ligands are immobilized onto a porous support. The support is assembled in a device that is adapted for multiple cycles of passage of the reagent solution through the porous support. A reagent solution is added to the device and passes through the porous support. During the process, the reagent binds the ligand. The passage/binding process is repeated multiple times thereby the binding of the reagent and the ligand is greatly enhanced.

When multiple ligand-bound supports are stacked and used, the invention provides a method for detecting ligands in multiple samples.

The invention is also directed to a device comprising means of generating multiple cycles of solution passing through a porous support. A device comprise a support holder, which when holds a ligand support divides the device into a first compartment and a second compartment; one or more pumps to drive reagent solution through said support; and means to transfer reagent solution from one compartment to the other.

DESCRIPTION OF THE PREFERRED EMBODIMENTS

Figure 1:
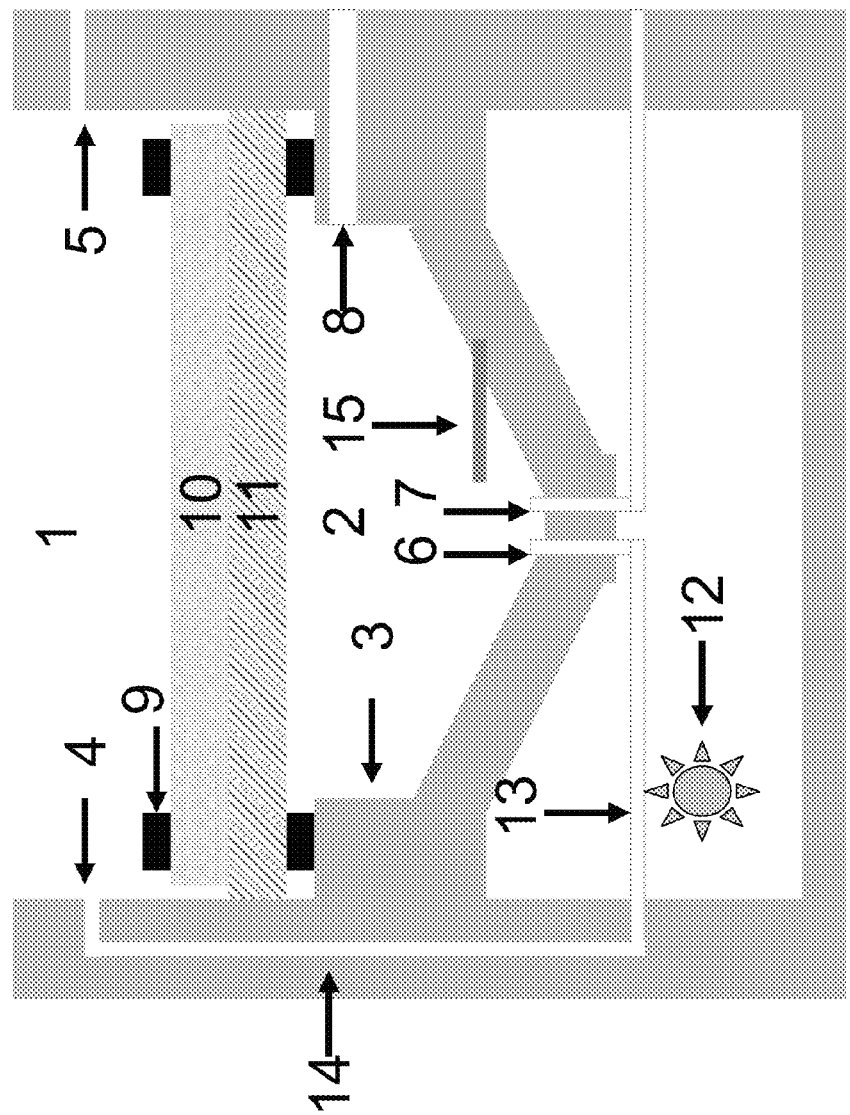
FIG. 1 illustrates a device according to one embodiment of the present invention.
Figure 2:
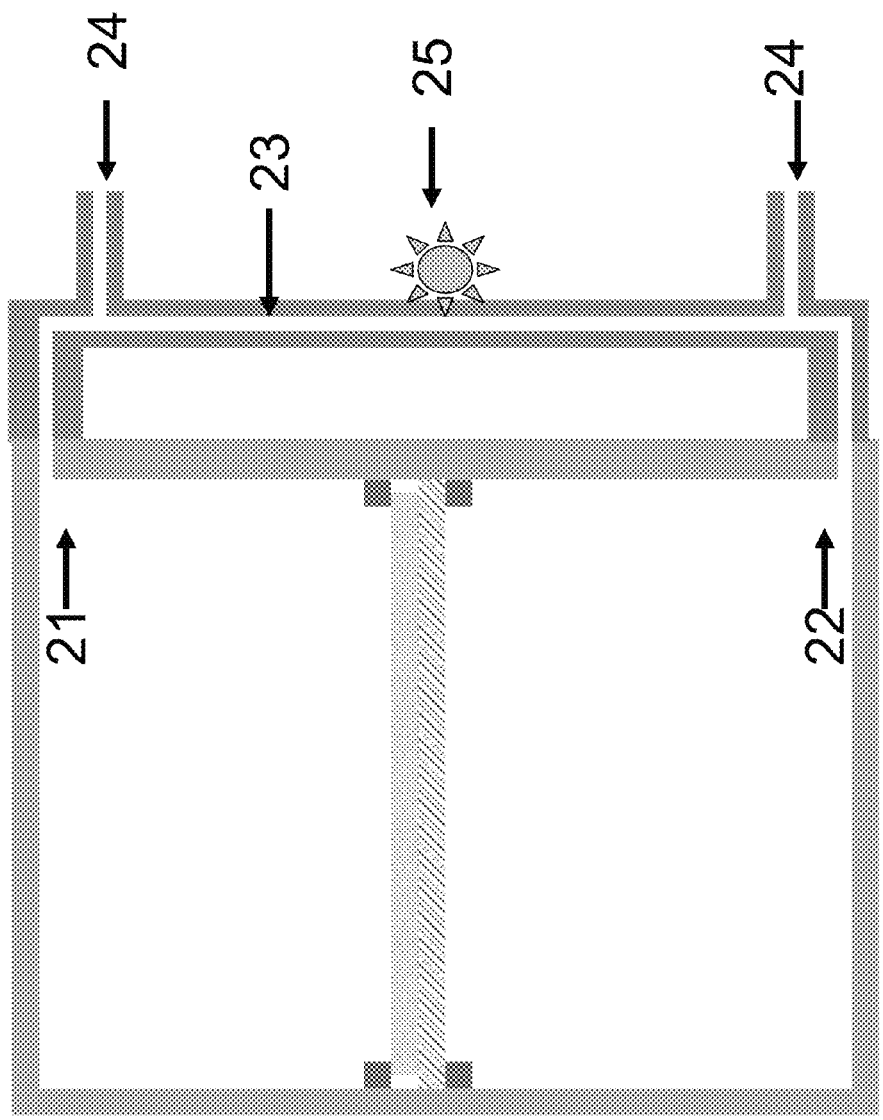
FIG. 2 illustrates a device according to another embodiment of the present invention.

The present invention provides a method and a device to facilitate the binding of reagents in a solution to ligands immobilized on a porous support. The term "reagents" as used herein refers to biological molecules, such as antibodies, recombinant proteins, synthesized peptides, DNA, RNA, nucleotides, and small chemicals.

The term "ligands" are used to refer biological molecules, including but not limited to proteins. For the purpose of the specification and claims, ligands refer to molecules that interact with reagents; and ligands are usually immobilized on a porous ligand support.

The term "ligand support" is used herein, for the purposes of the specification and claims, to mean a solid structure on which ligands are immobilized. Ligand supports are usually porous, that is they contain pores, maybe microscopic pores through which a solution can pass through. Many types of porous ligand support are widely used and the methods to make and use them are known in the arts. In the preferred embodiments, the porous ligand supports are membranes made of nitrocellulose, nylon, polyvinylidene difluoride (PVDF), or their derivatives.

The term "immobilization" is used herein, for the purpose of the specification and claims, to mean the restriction of a ligand on a ligand support so that the movement of the ligand on the support is limited. For example, when an antibody is immobilized on a membrane support, the antibody is attached to the membrane so that it may not dissociate from the membrane and the movement of the antibody on the membrane is also limited. Methods are available for immobilizing ligands on ligand supports, such as those described by Lehrach, et al. (Hybridization fingerprinting in genome mapping and sequencing, genome analysis, Vol. 1, Davies and Tilgham, Eds, Cold Spring Harbor Press, pp. 39-81, 1990) and Brown et al. (U.S. Pat. No. 5,807,522). Each of the aforementioned articles is incorporated by reference in its entirety for all purposes. The immobilization of ligands can be via covalent link or non-covalent link by adsorption or entrapment (Trevan, 1980, Immobilized Enzymes: an introduction and their application in biotechnology. Wiley, Chichester).

In general the present method involves the multiple cycles/passages of a reagent solution through a ligand-immobilized porous support using a cycling/repeated routine. During each cycle, the reagent solution passes through the porous support via a filtration-like process; then the solution is collected to pass the ligand support again in the next cycle. During each passage only a fraction of the reagent have the chance of interacting with the ligands. This is partly due to the fact that in most cases (e.g. a Western blot) ligands are present at only part of the porous support; and the passage of reagent solution is through the whole ligand support. Therefore, one passage is insufficient for maximum binding. The present method uses repeated passages of the reagent solution through the porous support and dramatically increases the chance of reagents interacting with the ligands. The present method uses a filtration-like process except that here the process is not to separate solid particles from fluids but to facilitate antibody-antigen interaction.

For the purposes of the specification and claims, the term "number of passage" is used herein, to describe the times/cycles that a solution is passed through a ligand support. The optimal number of passage varies, depending on specific reagent-ligand binding. In a preferred embodiment, the number of passage ranges from 2 to 1000. In another preferred embodiment, the number of passage ranges from 5 to 100. In another preferred embodiment, the number of passage ranges from 10 to 50.

In another preferred embodiment, the passage of a solution through a ligand support and the return of the passed solution for filtration can occur simultaneously for a period that a desired number of passages are achieved.

In the present method, the passage of a reagent solution through the ligand support can be driven by a negative pressure or a positive pressure, or a combination of the two. Negative pressure and positive pressure can be generated by pumps based on a variety of principles. The speed of reagent solution passing through the ligand support can be controlled. Slow passing can be used for some reagent-ligand bindings; and fast passing can be used for other reagent-ligand bindings. Flow rate can be from 1 to 1000 ml per square centimeter per minute. In one preferred method, 10 to 50 ml of solution is passed through a 100 square centimeter support in 1 minute. The flow rate can be adjusted by many known means. The procedure can be performed at room temperature or at 4 degree Celsius.

In the preferred method, a cycling device is used to facilitate the cycling process. The preferred cycling devices (see FIGS. 1-4) comprise means of passing a reagent solution through a porous ligand support and transferring of the reagent solution from one side of the support to the other side for the next passage; and repeating the process. A device (FIG. 1) according to the present invention may comprise several features: a first compartment 1, a second compartment 2, and a ligand support holder 3. When a ligand support is placed in the holder, the ligand support and the holder will separate the first and the second compartments. For the purpose of description, the first compartment can be regarded as an upper compartment; and the second compartment can be regarded as a lower compartment. In practice the features described for these two compartments may be interchangeable. Two or more of these features can be embodied in the same physical component.

The upper compartment is usually open to the outside. It contains an inlet 4 where a reagent solution is drawn in from the lower compartment. The upper compartment may contain additional inlet(s) 5 that other solutions can be flown in.

The upper compartment may contain other features, such as a lid with or without an opening.

The lower compartment is usually closed to the outside during operation so that negative or positive pressure can be established to drive the solution from the upper compartment to the lower compartment or vice verse, passing through the ligand support. The lower compartment is preferably tapered, narrower at the lower part away from the support, allowing the solution to be collected at the bottom. Tapered design is also helpful for even distribution of pressure. An outlet 6 is incorporated to allow reagent solution returning/cycling to the upper compartment. Another outlet 7 may be used for solution removal. Solution cycling and removal may use the same outlet. A separate outlet 8 can be used to establish negative pressure. The outlet 8 may be at a higher position than the cycling outlet 6. The inlets and outlets may incorporate pressure-sensitive mechanisms, such as pressure-activated gate or pressure-breachable seal. As shown in FIG. 1, the outlets for cycling and solution removal preferably located at the lowest point in the lower compartment of the device. The outlets are preferably set apart from the ligand support by a small distance to allow even flow of the solution across the support.

The ligand support holder typically has a gasket area 9 designed to establish a seal needed for the vacuum or positive air pressure that drives the filtration-like process. The seal also makes sure that all reagent solution will pass through the ligand support but not other areas, such as peripheral leakage.

In another preferred embodiment, the cycling device further comprises one or more backing. A backing is a supporting structure that is placed under a ligand support. In practice, the support holder will hold a ligand support 10 as well as one or more backings 11. The backing can be a screen to provide rigidity to an otherwise non-rigid ligand support. The backing allows free flow of fluid through it. The backing is usually made from materials that have no binding to the reagent in the solution, including but are not limited to PTFE membranes, hydrophobically coated membranes and the like (see U.S. Pat. Nos. 5,792,425 and 5,141,639). Backing can also act as buffer zone for evenly distributing reagent solution across the support area. The backing usually has a larger pore size than the ligand support. The pore size of the backing is preferably from 5 micron to 1 millimeter. The height of the backing can vary from a few microns to a few centimeters, preferably from 0.5 mm to 10 mm. In another embodiment, a backing is placed on top of a ligand support has a pore size smaller than that of the ligand support. The smaller pore size is necessary to prevent unwanted insoluble materials that may be present in a solution from contacting ligand support and clogging its pores.

The passage of solution through a support can be driven by a negative or a positive pressure. In one preferred embodiment, the negative pressure in the lower compartment is generated by a vacuum pump, which is connected to the lower compartment via an outlet. A dedicated outlet 8 may be used for vacuum. In a preferred embodiment, an outlet is built in the lower compartment, at a position below the support but at a higher position than the cycling outlet. The vacuum pump connected to the outlet can generate required vacuum to pull the reagent solution through ligand-immobilized support.

In another preferred embodiment, a solution is driven through the ligand support by positive pressure in the upper or lower compartment. For example, a positive pressure can be generated in the upper compartment using an air pump to drive the solution downward through the ligand support to the lower compartment. Air pump can be connected to the upper compartment via an air line which is in turn connected to an inlet in the upper compartment. Compartment may have a closed structure in order to keep a positive pressure. Both negative and positive pressure can be regulated by known means.

A reagent solution can be manually transferred from one compartment to the other during the cycling process. However, in preferred embodiments, automated means are used to generate cycling operation. In a preferred embodiment, a channel 14 and a pump 12 are used in the instant teaching to facilitate multiple cycles of reagent solution passage through ligand support. One end of the channel is connected to the inlet of the first compartment and the other end connected to the outlet of the second compartment. After passing through a ligand support, a reagent solution will be collected in the second compartment and cycled through the channel to the first compartment. The channel can be a built-in feature of the device compartments or a tubing connected to the inlet and outlet. In one embodiment, a peristaltic pump tubing is used as the channel and the peristaltic pump is used to propel the solution through the channel. One end of the pump tubing 13 is connected to the outlet of the lower compartment; and the other end of the pump tubing is connected to the inlet of the upper compartment. When the pump is in operation, the solution/air is driven out of the lower compartment and into the upper compartment; the negative pressure generated in the lower compartment will drive the solution in the upper compartment through the ligand support and into the lower compartment, then the solution is cycled to the upper compartment. The process continues until the pump is off.

In a preferred embodiment, the device according to the present invention contains means 15 to measure liquid level and/or amount accumulated in the lower compartment. There are many methods and devices available in the prior arts that can measure liquid level. Level sensors based on several principles can be used.

In one preferred embodiment, a reagent solution is added to the upper compartment of the device. When all or most of the reagent solution passes through the ligand support into the lower compartment, the reagent solution is returned to the upper compartment manually or by a pump. Then the reagent solution again is moved to pass the ligand support again. The process is repeated until desired number of passage is achieved. In this embodiment, passage of reagent solution through ligand support and the return of the reagent solution to the other compartment are followed by one another. In another preferred embodiment, the passage of a reagent solution through ligand support and the return of the reagent solution to the other compartment occur simultaneously. That is, any reagent solution having passed the ligand support is collected and returned to the upper compartment immediately for the next passage. A peristaltic pump or a combination of a peristaltic pump and a vacuum pump can be used to achieve this continues solution passage, collection and return. When the total volume of a solution has passes through the ligand support, one passage is achieved. When two times of the volume of the solution pass through the ligand support, two passages is achieved. In a preferred embodiment, the number of passage ranges from 2 to 1000. In another preferred embodiment, the number of passage ranges from 5 to 100. In another preferred embodiment, the number of passage ranges from 5 to 50.

In a typical test using the instant device, proteins of a cell lysate (ligand) were separated by SDS/PAGE and transferred to a PVDV membrane (ligand support). The membrane was pre-cut to proper size and placed on a screen (backing). The membrane and the screen were placed in the support holder of the device of FIG. 1. An antibody solution (reagent solution) is first added to the upper compartment; then a vacuum pump connect to the vacuum outlet of the lower compartment is used to generate vacuum to draw the antibody solution from the upper compartment to the lower compartment through the blot membrane. The antibody solution is accumulated at the bottom of the lower compartment. A peristaltic pump is used to pump the antibody solution to the upper compartment. The process is repeated until desired binding of antibody to its antigen on the blot is achieved. The vacuum pump and the peristaltic pump can be operated simultaneously so the cycling process is continuous: antibody solution is drawn through the blot membrane and recycled to the upper compartment.

In another embodiment of the present invention, the device (FIG. 2) according to the instant teaching has one inlet 21 at the upper compartment and one outlet 22 at the lower compartment. The inlet and outlet are connected by a channel 23 (e.g. a peristaltic pump tubing). Reagent solutions are pumped out of the lower compartment via the outlet; flow through the channel, and into the upper compartment via the inlet. The channel may be connected to other inlets/outlets 24 for adding/removing solutions. Valves can be used in these inlets/outlets for proper control.

Figure 3:
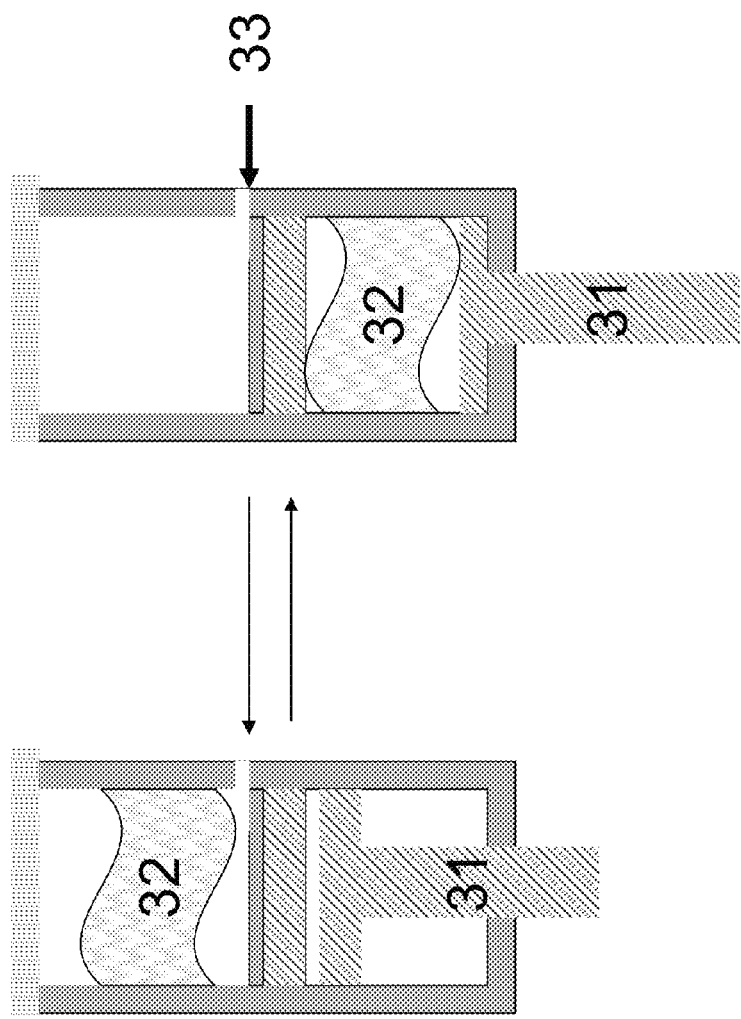
FIG. 3 illustrates a device using a piston pump for cycling according to an embodiment of the present invention.
Figure 4:
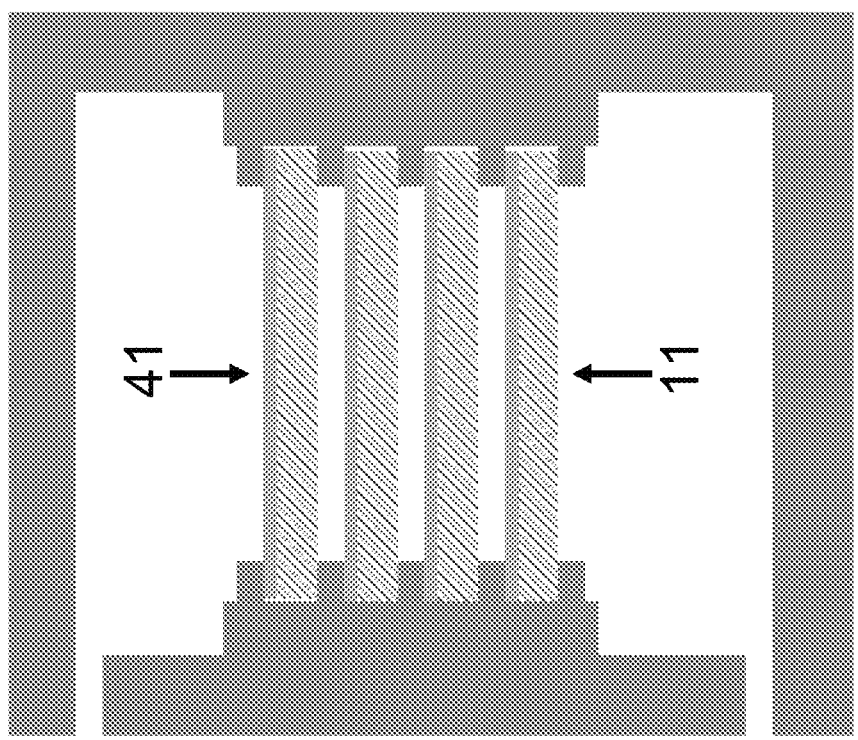
FIG. 4 demonstrates the assembly of multiple ligand-immobilized porous membranes in a device according to a preferred embodiment of the present invention.

In another embodiment of the present invention, a device uses a piston pump to produce cycles of reagent solution passing through ligand support (FIG. 3). Piston pump 31 can be placed at the lower compartment and/or upper compartment to produce negative and/or positive pressure to induce the passage of reagent solution 32 through the ligand-bound porous support. Varieties of piston pumps in the known art can be used in the present method. Piston pumps can be part of the compartments; or can be connected to the compartments via inlet/outlet. Solutions can be added/removed from top or through an inlet/outlet 33.

The present invention also provides a method for simultaneous binding of a reagent to its interacting ligands on multiple porous supports. In a preferred method (FIG. 4), multiple ligand-immobilized supports 41 are stacked and placed in a device according to the instant teaching; reagent solution is brought into the compartment (i.e. through an inlet) and passes through each ligand support layer sequentially prior to being collected in the other compartment. The reagent solution then undergoes additional cycles of passing through the ligand support until desired binding is achieved. When reagent is over abundant than the ligands on the supports, such "serial-flow" allows near identical binding conditions for ligands on all supports.

In a preferred method, one or more backings 11 are used to separate the ligand supports. The backing provides rigidity. It can also act as buffer zone for evenly distributing reagent solution across the support area. The backing is usually a filter made from materials that has no binding to the reagent in the solution, for example, filter papers from Whatman.

In an example of the present method, a rectangular shaped porous membrane is used as the ligand support; and antibodies are deposited on it as circular dots. The antibodies can also be deposited in other shapes such as a rectangular shape of a few microns to a few centimeters wide and a few microns to a few centimeters long. The antibody-deposited membrane is placed in a small device having an upper and a lower compartment separated by the membrane; and means for cycling. The kit (device and the membrane) can be used in detecting antigens (e.g. a viral protein) according to present invention for clinical applications.

In another example of the present method, an array of antibodies are immobilized on a porous ligand support (e.g. nitrocellulose membrane), each at a predefined position so that each antibody can be identified by a specific position on the membrane.

In another example of the present method, proteins can be first separated and then transferred and immobilized on a support. The separation can be by gel electrophoresis according to proteins' molecular weight or isoelectric point. Sodium dodecyl sulphate-polyacrylamide gel electrophoresis (SDS-PAGE) and two-dimensional gel electrophoresis are often used.

In another example, proteins are separated by SDS/PAGE gel and transferred to a PVDF membrane. Five such membranes are stacked and placed in the holder of a device of the present invention. Each PVDF membrane is separated by two Whatman filter papers.

The cycling method and device described here not only can be used for improved binding of a reagent to its ligand, but also for other purpose. For example, after reagent-ligand binding, washing solution can be applied to a device according to the present invention and undergoes multiple cycles of passing through the ligand support to remove an unbound reagent from the support; thus reducing background signals of the assay.

Other modifications of the above-described embodiments of the invention which are obvious to those of skill in the area of molecular biology and related disciplines are intended to be within the scope of the following claims.

The invention claimed is:

1. A method to facilitate the binding of a reagent to a ligand, comprising the steps of
    1. immobilizing said ligand on a porous ligand support;
    2. placing said ligand support in a cycling device to divide said device into two compartments, a first compartment and a second compartment;
    3. adding said reagent in solution in said first compartment;
    4. passing said reagent solution through said support into said second compartment, whereby some of said regent bind to the ligand on said qupport;
    5. transferring said reagent solution from said second compartment to said first compartment;
    6. repeating the steps of 4 and 5 until a desired number of passages of reagent solution through said ligand support is achieved.

2. The method of claim 1, wherein said desired number of passage ranges from 2 to 1000.

3. The method of claim 1, wherein said desired number of passage ranges from 5 to 100.

4. The method of claim 1, wherein said desired number of passage ranges from 10 to 50.

5. The method of claim 1, wherein a peristaltic pump is used to transfer said reagent solution from said second compartment to said first compartment.

6. The method of claim 1, wherein a peristaltic pump is used to generate vacuum to move said reagent solution through said ligand support.

7. The method of claim 1, wherein a peristaltic pump is used to transfer said reagent solution from said second compartment to said first compartment; and a separate vacuum pump is used to generate vacuum to move said reagent solution through said ligand support.

8. The method of claim 1, wherein a piston pump is used to drive said reagent solution through said ligand support.

9. The method of claim 1, wherein two piston pumps are used to drive said reagent solution through said ligand support, one pump in said first compartment and one pump in said second compartment.

10. The method of claim 1, wherein two or more ligand supports are stacked together.

11. The method of claim 1, wherein five or more ligand supports are stacked together.

12. The method of claim 11, wherein said ligand supports are separated by one or more backings.

13. The method of claim 1, wherein said support is an immunoblot membrane.

14. The method of claim 1, wherein said reagent is an antibody.

15. The method of claim 1, further comprising the step of placing one or more backings under said ligand support.

16. A cycling device to pass a reagent solution through a ligand support multiple times, comprising:
a supply of reagent in operative connection with a ligand support wherein said ligand support divides said device into a first compartment and a second compartment;
one or more pumps to pass said reagent solution from said first compartment to said second compartment through said ligand support, and to transfer said reagent solution from said second compartment to said first compartment.

17. The cycling device of claim 16, wherein said first compartment contains an inlet, said second compartment contains an outlet, said inlet and outlet are connected via a channel.

18. The cycling device of claim 16, wherein one of said pumps is a vacuum pump to move said reagent solution through said ligand support.

19. The cycling device of claim 16, wherein said device contains means to measure reagent solution in said second compartment.

20. The cycling device of claim 16, wherein said second compartment contains two outlets, one for vacuum and the other one for solution cycling and/or removal.

* * * * *